US010960115B2

(12) United States Patent
Chua

(10) Patent No.: US 10,960,115 B2
(45) Date of Patent: Mar. 30, 2021

(54) MANUAL BREAST PUMP AND METHOD OF USE

(71) Applicant: Poh Leng Jeffrey Chua, Singapore (SG)

(72) Inventor: Poh Leng Jeffrey Chua, Singapore (SG)

(*) Notice: Subject to any disclaimer, the term of this patent is extended or adjusted under 35 U.S.C. 154(b) by 244 days.

(21) Appl. No.: 16/132,362

(22) Filed: Sep. 15, 2018

(65) Prior Publication Data
US 2020/0086019 A1 Mar. 19, 2020

(51) Int. Cl.
*A61M 1/06* (2006.01)

(52) U.S. Cl.
CPC ....... *A61M 1/064* (2014.02); *A61M 2205/071* (2013.01)

(58) Field of Classification Search
CPC ...... A61M 1/0072; A61M 1/06; A61M 1/064; A61M 2205/0216; A61M 2205/071; A61M 2205/075
See application file for complete search history.

(56) References Cited

U.S. PATENT DOCUMENTS

| D62,963 S | 8/1923 | Sandford |
| D258,626 S | 3/1981 | Dembicks et al. |
| D285,884 S | 9/1986 | Wise et al. |
| D313,103 S | 12/1990 | Kawano |
| D326,516 S | 5/1992 | Chambers |
| 5,370,622 A | 12/1994 | Livingston et al. |
| D372,777 S | 8/1996 | Kan |
| 5,776,098 A | 7/1998 | Silver et al. |
| D408,528 S | 4/1999 | Kan |
| D408,625 S | 4/1999 | Barker |
| D418,598 S | 1/2000 | Jauch |
| D427,425 S | 7/2000 | Stahl |
| D457,307 S | 5/2002 | Pukall et al. |
| 6,702,167 B2 | 3/2004 | Annis |
| D561,021 S | 2/2008 | DuVal et al. |
| D583,985 S | 12/2008 | Warden et al. |
| D609,331 S | 2/2010 | Paterson et al. |
| D679,904 S | 4/2013 | Allan |
| D688,785 S | 8/2013 | Cudworth |
| D688,786 S | 8/2013 | Cudworth |
| D698,646 S | 2/2014 | Paredes et al. |

(Continued)

FOREIGN PATENT DOCUMENTS

| CA | 184104 | 9/2019 |
| CN | 303890343 | * 10/2016 |

(Continued)

OTHER PUBLICATIONS

Babytree: Manual Breast Pump listing: Retrieved from URL: http://www.babytree.com/commnity/club201400/topic_201912410html (Published on May 28, 2014). (Year: 2014).*

(Continued)

*Primary Examiner* — Deanna K Hall

(57) ABSTRACT

A manual breast pump is disclosed. The manual breast pump comprises a breast cup configured to engage with a mother's breast and a reservoir at a base of the breast cup configured to collect milk extracted from the mother's breast. The reservoir is defined by a wall. The wall comprises a varying thickness from a top of the reservoir toward a bottom of the reservoir.

13 Claims, 6 Drawing Sheets

(56) References Cited

U.S. PATENT DOCUMENTS

| | | |
|---|---|---|
| D699,110 S | 2/2014 | Cox et al. |
| D701,955 S | 4/2014 | Thomas |
| D702,040 S | 4/2014 | Bozzi |
| 8,845,604 B2 | 9/2014 | Croizat et al. |
| D730,048 S | 5/2015 | Muller et al. |
| D731,180 S | 6/2015 | Neuhaus |
| D783,803 S | 4/2017 | Rigert et al. |
| D808,006 S | 1/2018 | Zhang |
| D810,925 S | 2/2018 | Zhang |
| 10,016,566 B2 | 7/2018 | Zhang |
| D826,545 S | 8/2018 | Brothers |
| D826,546 S | 8/2018 | Brothers |
| 10,264,862 B2 | 4/2019 | Makuyana et al. |
| D847,490 S | 5/2019 | Pernefeldt et al. |
| D871,566 S | 12/2019 | Zhang |
| D874,126 S | 2/2020 | Peters |
| D874,815 S | 2/2020 | Wells |
| 10,716,882 B2 | 7/2020 | Evans et al. |
| 10,744,243 B2 | 8/2020 | Rigert et al. |

FOREIGN PATENT DOCUMENTS

| | | | |
|---|---|---|---|
| CN | 303890343 S | | 10/2016 |
| CN | 302890427 S | | 11/2016 |
| CN | 303890427 | * | 11/2016 |

OTHER PUBLICATIONS

Funny Baby: Eight Yuan poly cost-effective full silicone natural breast pump; retrieved from URL: http://product.800400.net/detail/7816236.html (Published on Dec. 18, 2014). (Year: 2014).*

Chua, Poh Leng, Jeffrey, Chinese Design Patent Application entitled "Silicone Breast Pump", filled on May 4, 2018, Serial No. 201830197234.9.

Babytree: Manual Breast Pump Listing; Retrieved from URL: http://www.babytree.com/commnity/club201400/topic_201912410.html (published on May 28, 2014).

Funny Baby: Eight Yuan poly cost-effective full silicone natural breast pump; retrieved from URL: http://product.800400.net/detail/7816236.html (published on Dec. 18, 2014).

Chua, Poh Leng, Jeffrey, Patent Application entitled "Breast Milk Collection and Storage System and Method of Use", filed Aug. 26, 2019, U.S. Appl. No. 16/551,461.

Restriction Requirement dated Jun. 24, 2020, U.S. Appl. No. 29/663,465, filed Sep. 15, 2018.

Restriction Requirement dated Aug. 27, 2020, U.S. Appl. No. 29/703,314, filed Aug. 26, 2019.

Notice of Allowance dated Oct. 2, 2020, U.S. Appl. No. 29/703,314, filed Aug. 26, 2019.

* cited by examiner

MANUAL BREAST PUMP AND METHOD OF USE

BACKGROUND

Nursing mothers often use breast pumps to express milk from their breasts for bottle feeding their infant children. Breast pumps may be manually or electrically operated.

SUMMARY

In one embodiment of the disclosure, a manual breast pump is disclosed. The manual breast pump comprises a breast cup configured to engage with a mother's breast and a reservoir at a base of the breast cup configured to collect milk extracted from the mother's breast. The reservoir is defined by a wall. The wall comprises a varying thickness from a top of the reservoir toward a bottom of the reservoir.

In another embodiment of the disclosure, a manual breast pump is disclosed. The manual breast pump comprises a breast cup configured to engage with a mother's breast and capable of being reshaped from an initial shape to a folded shape. The breast cup is capable of being returned to the initial shape after a portion of the breast cup is engaged with the mother's breast. The manual breast pump also comprises a reservoir at a base of the breast cup configured to collect milk extracted from the mother's breast.

In yet another embodiment of the disclosure, a method of using a manual breast pump is disclosed. The method comprises engaging a breast cup of the manual breast pump with a mother's breast and compressing and releasing a reservoir of the breast pump at a first location to create a first suction force to extract milk from the mother's breast into the reservoir. The method also comprises compressing and releasing the reservoir at a second location to create a second suction force to extract milk from the mother's breast into the reservoir. The first suction force and the second suction force are different.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1A:
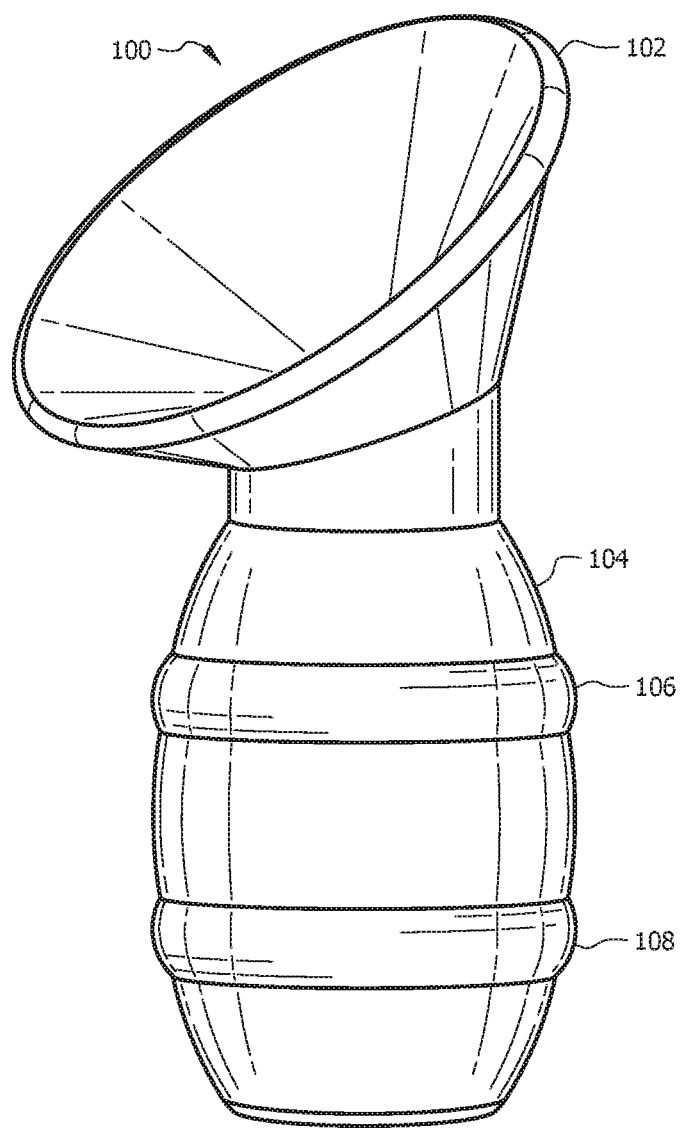
FIG. 1A illustrates a perspective view of a manual breast pump according to an embodiment of the disclosure.
Figure 1B:
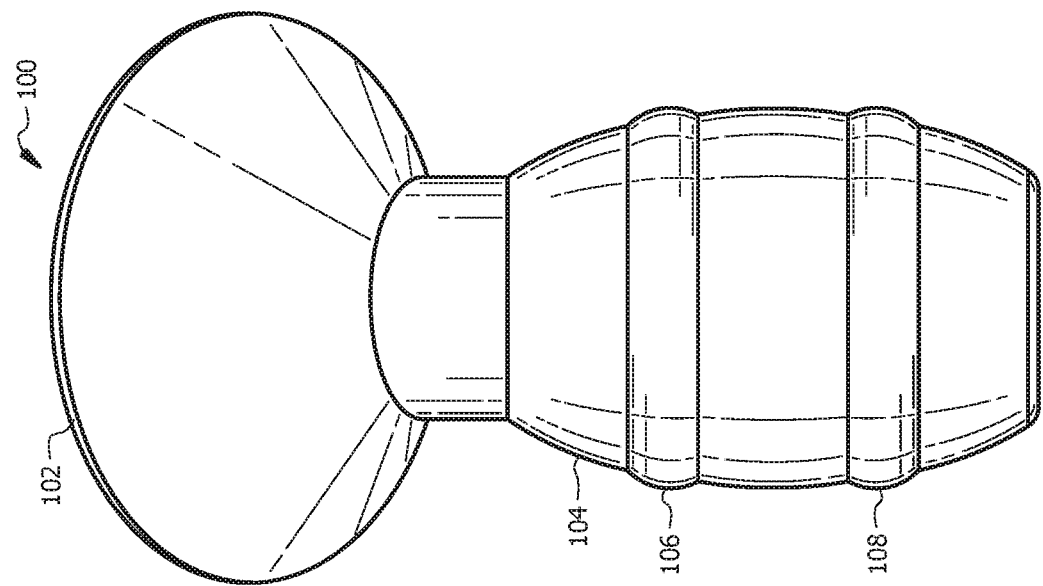
FIG. 1B illustrates a front view of a manual breast pump according to an embodiment of the disclosure.
Figure 1C:
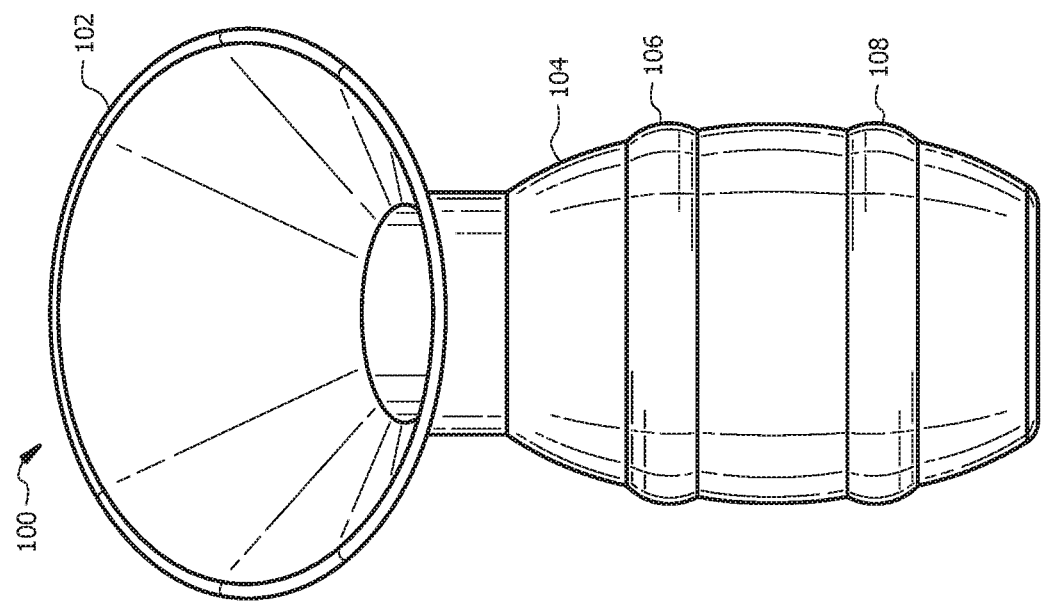
FIG. 1C illustrates a back view of a manual breast pump according to an embodiment of the disclosure.
Figure 1D:
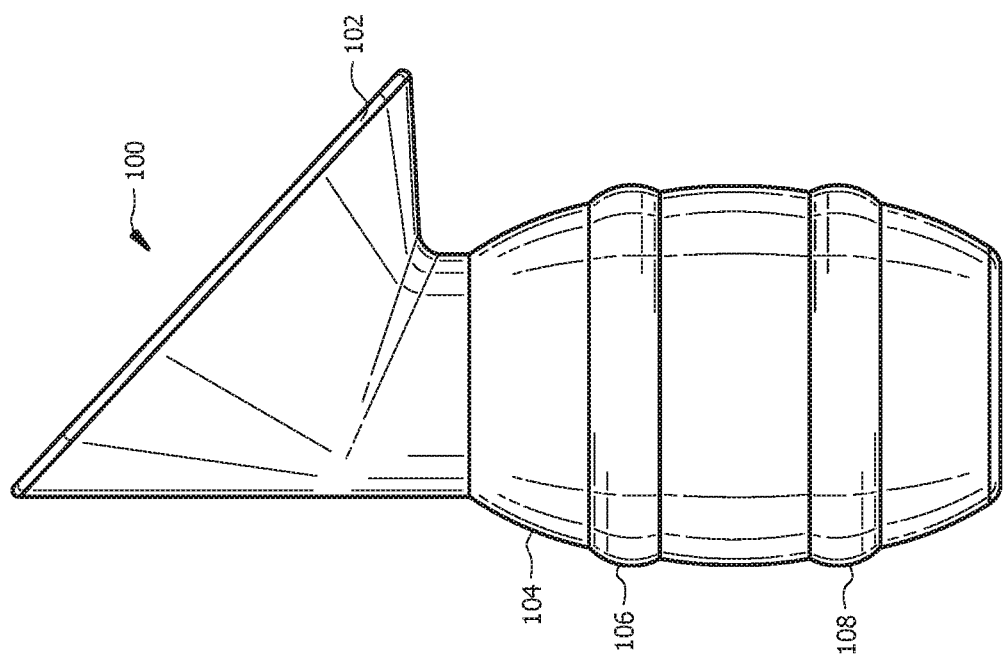
FIGS. 1D and 1E illustrate side views of a manual breast pump according to an embodiment of the disclosure.
Figure 1E:
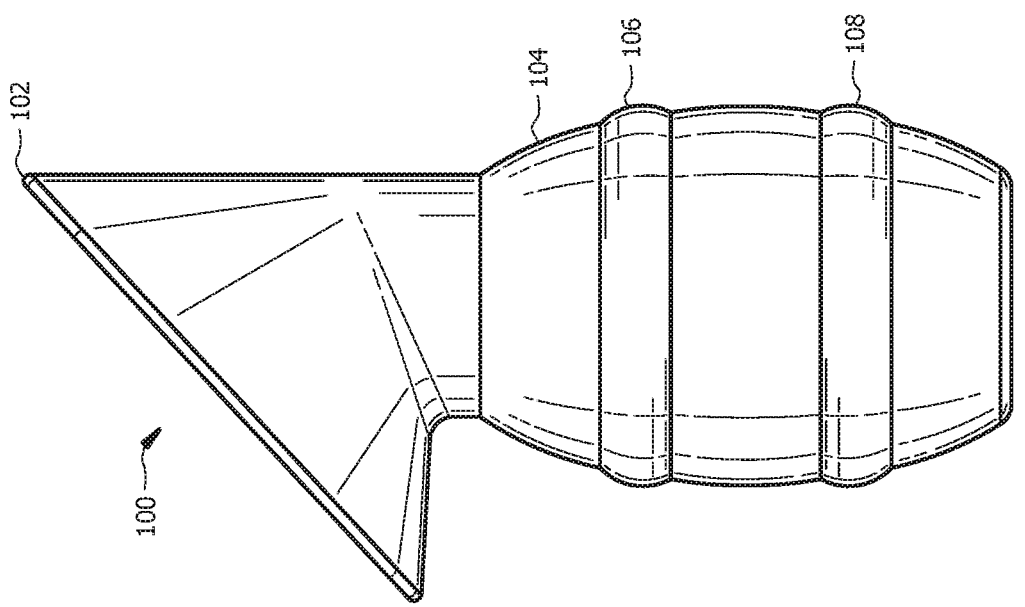

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The pending application is directed to a manual breast pump that can apply varying pressure or suction force to a mother's breast. The manual breast pump comprises a breast cup and a reservoir at the base of the breast cup. The variable suction force is enabled by a varying thickness of the wall of the reservoir from a top of the reservoir toward a bottom of the reservoir, optionally along with one or more rings or protrusions in the wall of the reservoir. More particularly, when the breast cup is engaged with a mother's breast, the varying thickness of the wall of the reservoir provides varying pressure or suction force to a mother's breast depending on where the reservoir is compressed and released.

The difference in the volume of air in the reservoir before and after the reservoir 104 is compressed creates a suction force. A thinner wall may be easier to compress, which may create a greater difference in volume of air and consequently a stronger suction force. In contrast, a thicker wall may be harder to compress, which may create a lesser difference in volume of air and consequently a lesser suction force.

The wall of the reservoir of the manual breast pump disclosed herein may be thickest toward the bottom of the reservoir and thinnest toward the top of the reservoir with a gradual thickening of the wall from the top of the reservoir toward the bottom of the reservoir. Such a configuration creates the strongest suction force when the reservoir is compressed and released toward the top of the reservoir because the wall of the reservoir is thinnest toward the top, creates the weakest suction force when the reservoir is compressed and released toward the bottom of the reservoir because the wall of the reservoir is thickest toward the bottom, and creates a decreasing suction force as the reservoir is compressed and released at points moving down the reservoir from the top of the reservoir because there is a gradual thickening of the wall of the reservoir from the top of the reservoir toward the bottom. While described as having the thickest part of the wall at the bottom, the graduation of the thickness could also be reversed such that the wall is thickest at the top and thinnest at the bottom in some embodiments.

The reservoir may optionally comprise one or more rings around the perimeter of the reservoir to add thickness to the wall of the reservoir. For example, there may be a ring towards the bottom of the reservoir. The wall of the reservoir including such a ring may comprise the thickest cross-section of the reservoir at the ring to prevent the bottom of the reservoir from being deformed after the reservoir is compressed.

The manual breast pump disclosed herein may also comprise a breast cup that is capable of being reshaped. For example, the breast cup may be folded before cupping onto the mother's breast. Once a portion of the breast cup is engaged with the mother's breast, the breast cup may be flipped back to its original shape to cup the mother's breast while the reservoir is compressed, which produces a firmer breast cupping effect onto the breast. A firmer breast cupping effect allows a minimal amount of air to escape from the breast pump, thereby creating a stronger suction force.

Turning now to FIGS. 1A-1E, an embodiment of a manual breast pump 100 having a breast cup 102 and a reservoir 104 is illustrated. The breast cup 102 may be shaped so as to enclose a volume defining the reservoir 104 used to receive and store any expressed milk. The breast cup 102 may comprise a funnel shape, cone shape, or another shape to engage with a mother's breast. The reservoir 104 may comprise a rounded shape to allow the restoring forces to restore the initial shape of the reservoir 104 when it is compressed. In some embodiments, the reservoir 104 may comprise a cylindrical shape, a spherical shape, a bulbous shape, a square shape, or another shape. The bottom of the reservoir 104 may have a flat surface to allow the breast pump 100 to be freestanding when placed on a flat surface.

In an embodiment, the reservoir 104 is at a base of the breast cup 102. The breast cup 102 and the reservoir 104 may be formed as a single unit (e.g., an integrated structure, etc.). A single unit manual breast pump is simpler and has fewer parts, making it easier to use and clean. In an alternative embodiment, the breast cup 102 and the reservoir 104 may be individual components coupled together.

The breast cup 102 and the reservoir 104 may be made of pliable material such as a polymer. Various food grade polymers can be used such as silicone. The material used to form the breast pump 100 may have any color or patterns as desired, and in some embodiments may be clear. This may allow the volume of collected milk to be easily determined, for example, by using markings or graduations on the interior or exterior of the reservoir 104 to measure the volume.

In an embodiment, the polymer can be capable of being reshaped. As will be discussed in further detail below with respect to FIG. 3, the breast cup 102 may be capable of being reshaped. With respect to the reservoir 104, the reservoir 104 comprises an initial shape and the reservoir 104 may be capable of being compressed and released and return to the initial shape.

In an embodiment, the breast cup 102 can be applied to a mother's breast to expel milk from the breast to the reservoir 104. Applying the breast cup 102 to the breast and compressing and releasing the reservoir 104 creates an initial suction force to the mother's breast, which enables milk to be collected in the reservoir 104. For example, the breast cup 102 may be applied to a mother's breast and the reservoir 104 compressed and released to create an initial suction force. In some embodiments, the initial suction force created may catch milk during "let-down" or other breast milk leaks while a child nurses on her other breast.

In some embodiments, the reservoir 104 may continue to be compressed and released to create more suction force beyond the initial suction force to expel more milk. For example, the breast cup 102 may be applied to a mother's breast and the reservoir 104 compressed and released to create an initial suction force, and while the mother nurses a child on her other breast, the reservoir 104 may be compressed and released periodically to create more suction pressure to expel more milk beyond just milk during "let-down" or other breast milk leaks while the child nurses. Additionally or alternatively, the breast cup 102 may be applied to a mother's breast and the reservoir 104 compressed and released to create an initial suction force when mother is not nursing a child on her other breast, and the reservoir 104 may be compressed and released periodically to create more section pressure than just the initial suction force so as to expel milk from the breast.

In an embodiment, the reservoir 104 comprises one or more rings 106, 108 around the perimeter of the reservoir 104. For example, the reservoir 104 may comprise only a first ring 106, only a second ring 108, or both the first ring 106 and the second ring 108. In other embodiments, the reservoir 104 may comprise more than two rings. The rings may be made of silicone. For example, the rings 106, 108 (and any additional optional rings, etc.) can be integrally formed with the material of the reservoir 104. The rings 106, 108 will be discussed in further detail below with respect to FIG. 2.

Figure 2:
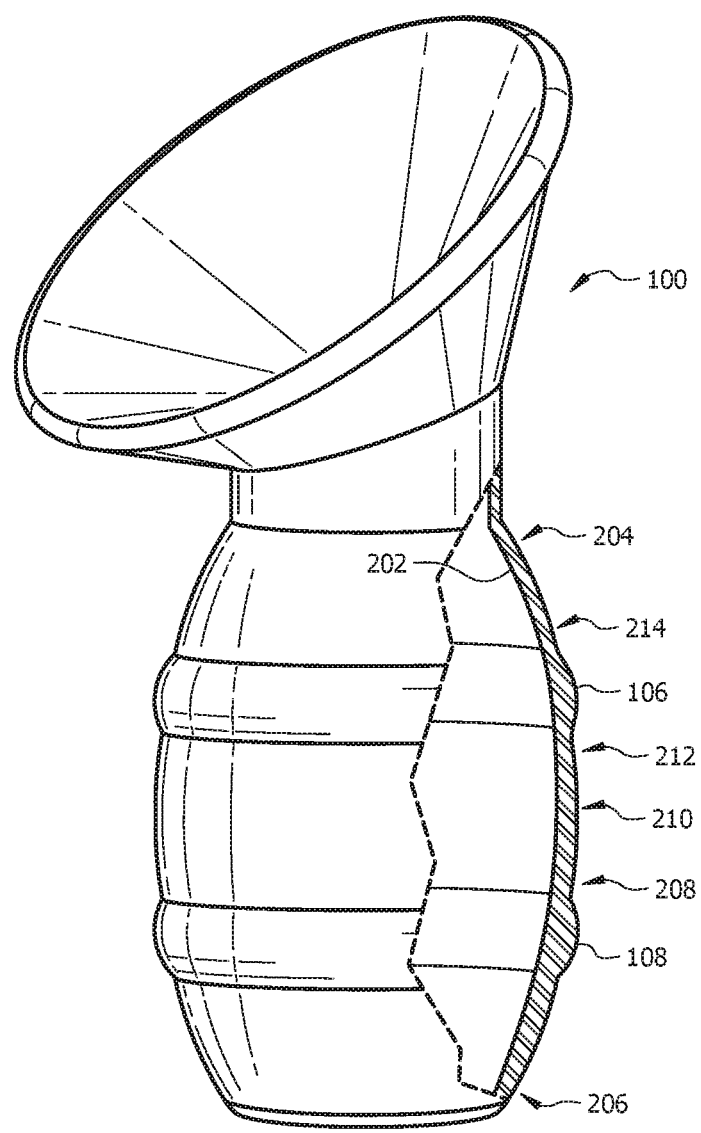
FIG. 2 illustrates a cross-sectional view of a manual breast pump according to an embodiment of the disclosure.

Turning to FIG. 2, a cross-sectional view of an embodiment of the manual breast pump 100 is disclosed. As illustrated in FIG. 2, the wall 202 of the reservoir 104 may comprise a varying thickness to create a varying suction force. For example, the wall 202 of the reservoir 104 may be thinnest towards a top 204 of the reservoir 104 and thickest towards a bottom 206 of the reservoir 104 with a gradual thickening of the wall 202 between the top 204 of the reservoir 104 and the bottom 206 of the reservoir 104.

The difference in the volume of air in the reservoir 104 before and after the reservoir 104 is compressed creates a suction force. A thinner wall (e.g., the wall 202 towards the top 204 of the reservoir 104) may be easier to compress, which may create a greater difference in volume of air and consequently a stronger suction force. In contrast, a thicker wall (e.g., the wall 202 towards the bottom 206 of the reservoir 104) may be harder to compress, which may create a lesser difference in volume of air and consequently a lesser suction force.

In an embodiment, as discussed above, the reservoir 104 may comprise one or more rings such as the first ring 106 and/or the second ring 108. The first rings 106 and/or the second ring 108 may add additional thickness to wall 202 of the reservoir 104 to help vary the suction force due to a changing restoring force. In an embodiment, the wall 202 including the second ring 108 can comprise the thickest cross-section of the reservoir 104 to prevent the bottom 206 of the reservoir 104 from being deformed after the reservoir 104 is compressed. For example, the thickness of the wall 202 including the second ring 108 may be between about 3.3 millimeters to about 4.5 millimeters thick, between about 3.6 millimeters to about 4.2 millimeters thick, between about 3.8 millimeters to about 4.0 millimeters thick, or another thickness.

In an embodiment, the thickness of the wall 202 decreases by about ten percent to about thirty percent from the second ring 108 to a first point 208 toward a middle 210 of the reservoir 104. For example, the thickness of the wall 202 may decrease by about twenty percent from the second ring 108 toward the first point 208 of the reservoir 104. The thickness of the wall 202 at the first point 208 may be between about 2.9 millimeters to about 3.3 millimeters, between about 3.0 millimeters to about 3.2 millimeters, or another thickness.

In an embodiment, the thickness of the wall 202 decreases between about five percent and about twenty percent from the first point 208 to a second point 212 toward the top 204 of the reservoir 104. For example, the thickness of the wall 202 may decrease by about ten percent from the first point 208 to the second point 212 of the reservoir 104. The thickness of the wall 202 at the second point 212 may be about 2.6 millimeters to about 3.0 millimeters, about 2.7 millimeters to about 2.9 millimeters, or another thickness.

In an embodiment, the thickness of the wall 202 decreases between about five percent and about twenty percent from the second point 212 to a third point 214 toward the top 204 of the reservoir 104. For example, the thickness of the wall 202 may decrease by about ten percent from the second point 212 to the third point 214 of the reservoir 104. The thickness of the wall 202 at the third point 214 may be between about 2.2 millimeters to about 2.7 millimeters, between about 2.4 millimeters to about 2.6 millimeters, or another thickness.

As discussed above, the difference in the volume of air in the reservoir 104 before and after the reservoir 104 is compressed creates a suction force due to a restoring force exerted by the walls of the reservoir 104. Thus, a thinner wall may be easier to compress and create a stronger suction force while a thicker wall may be harder to compress and create a lesser suction force. Compressing and releasing the reservoir 104 at the second ring 108 where the wall 202 is the thickest may result in a relatively small volume change that can create a gentle suction force that is less than the suction force created by compressing and releasing the reservoir 104 at another point on the reservoir closer toward the top 204 of the reservoir where a relatively larger volume change can be accomplished with the same compression force. Compressing and releasing the reservoir 104 at the middle 210 of the reservoir 104 where the wall 202 is thinner than the wall 202 at the second ring 108 may create a medium suction force that is greater than the gentle suction force created by compressing and releasing the reservoir 104 at the second ring 108, but less than the suction force created by compressing and releasing the reservoir 104 at another point on the reservoir 104 closer to toward the top 204 of the reservoir. Compressing and releasing the reservoir 104 toward the top 204 of the reservoir 104 where the wall 202 is thinner than the wall 202 at the middle 210 of the reservoir 104 may create a strong suction force which is greater than the medium suction force created by compressing and releasing the reservoir 104 at the middle 210 of the reservoir.

In an embodiment, the medium suction force created by compressing and releasing the reservoir 104 at the middle 210 of the reservoir 104 can be between about 5 percent and about 30 percent, between about 10 percent and about 25 percent, or about 20 percent greater than the gentle suction force created by compressing and releasing the reservoir 104 at the second ring 108. The strong suction force created by compressing and releasing the reservoir 104 toward the top 204 of the reservoir 104 may be between about 5 percent and about 30 percent, between about 10 percent and about 25 percent, or about 20 percent ten percent greater than the medium suction force created by compressing and releasing the reservoir 104 at the middle 210 of the reservoir 104.

Figure 3:
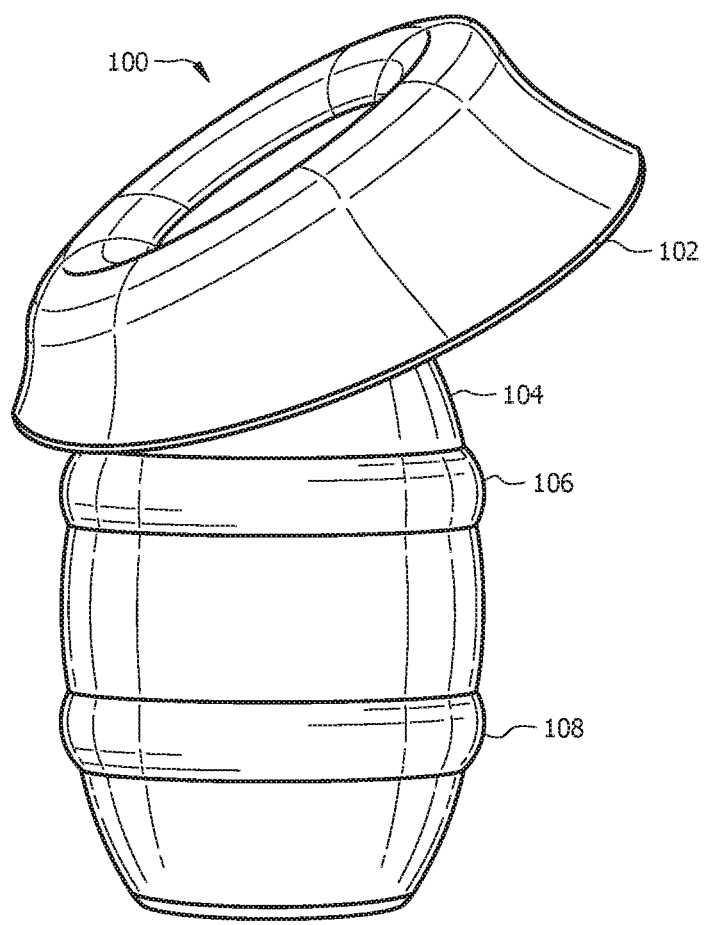
FIG. 3 illustrates a perspective view of a manual breast pump with a breast cup folded according to an embodiment of the disclosure.

Turning to FIG. 3, an embodiment of the manual breast pump 100 is disclosed. The breast cup 102 may be capable of being reshaped. As discussed above, the manual breast pump 100 may be made of a polymer that is capable of being reshaped. The degree to which the breast cup 102 can be reshaped can be varied such that the size of the outermost portion (e.g., the sealing surface) can be varied to provide a selective size for the breast cup 102. As illustrated in FIG. 3, the breast cup 102 may be folded down away from a mother's breast. For example, the breast cup 102 may be folded before cupping onto the mother's breast. Once a portion of the breast cup 102 is engaged with the mother's breast, the breast cup 102 may be flipped back to its original shape to cup the mother's breast while the reservoir 104 is compressed, which produces a firmer breast cupping effect onto the breast. A firmer breast cupping effect allows a minimal amount of air to escape from the breast pump 100, thereby creating a stronger suction force.

Figure 4:
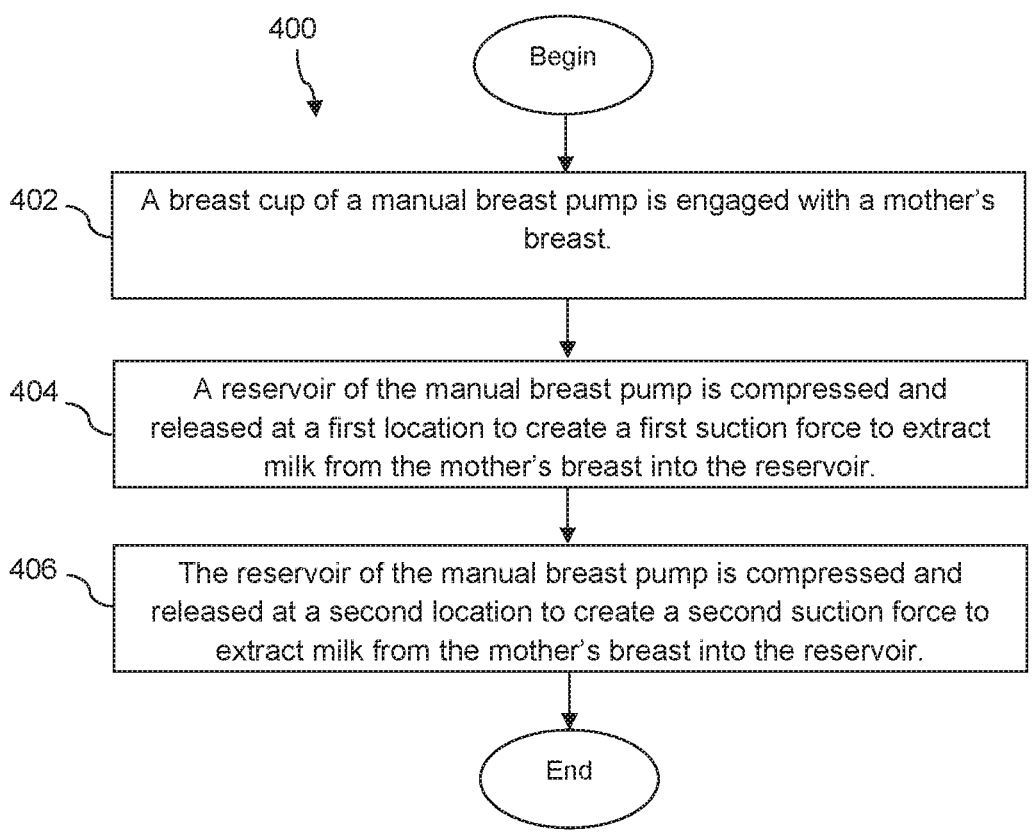
FIG. 4 illustrates a flow chart of a method according to an embodiment of the disclosure

Turning to FIG. 4, a method 400 is described. At block 402, a breast cup of a manual breast pump is engaged with a mother's breast. At block 404, a reservoir of the manual breast pump is compressed and released at a first location to create a first suction force to extract milk from the mother's breast into the reservoir. At block 406, a reservoir of the manual breast pump is compressed and released at a second location to create a second suction force to extract milk from the mother's breast into the reservoir. The first suction force and the second suction force are different.

In some embodiments, the breast cup 102 can be folded down prior to engaging the breast cup 102 with the mother's breast. The breast cup 102 may then be returned to its original shape after engaging the breast cup 102 with the mother's breast to create a firmer breast cupping effect onto the mother's breast and a stronger suction force.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A manual breast pump, comprising:
   a breast cup configured to engage with a mother's breast; and
   a reservoir at a base of the breast cup configured to collect milk extracted from the mother's breast, wherein the reservoir is defined by a wall, wherein the wall comprises a varying thickness from a top of the reservoir toward a bottom of the reservoir, wherein the wall of the reservoir is thickest toward the bottom of the reservoir and thinnest toward the top of the reservoir with a continuous gradual thickening of the wall from the top of the reservoir toward the bottom of the reservoir, wherein the reservoir comprises at least two rings around the outer perimeter of the reservoir to add thickness to the wall of the reservoir, wherein a ring of the at least two rings is located toward the bottom of the reservoir, and wherein the wall of the reservoir is thickest at the ring.

2. The manual breast pump of claim 1, wherein the breast cup and the reservoir are made of silicone.

3. The manual breast pump of claim 2, wherein the breast cup is made of silicone capable of being reshaped.

4. The manual breast pump of claim 2, wherein the reservoir comprises an initial shape, and wherein the reservoir is made of silicone capable of being compressed and released and returning to the initial shape.

5. The manual breast pump of claim 1, wherein the breast cup and the reservoir are formed as a single unit.

6. A manual breast pump, comprising:
   a breast cup configured to engage with a mother's breast and capable of being reshaped from an initial shape to a folded shape, wherein the breast cup is capable of being returned to the initial shape after a portion of the breast cup is engaged with the mother's breast; and a reservoir at a base of the breast cup configured to collect milk extracted from the mother's breast, wherein the reservoir is defined by a wall, wherein the wall of the reservoir is thickest toward a bottom of the reservoir and thinnest toward a top of the reservoir with a continuous gradual thickening of the wall from the top of the reservoir toward the bottom of the reservoir, wherein the reservoir comprises at least two rings around the outer perimeter of the reservoir to add thickness to the wall of the reservoir, wherein a ring of the at least two rings is located toward the bottom of the reservoir, and wherein the wall of the reservoir is thickest at the ring.

7. The manual breast pump of claim 6, wherein the breast cup and the reservoir are made of silicone.

8. The manual breast pump of claim 6, wherein the breast cup and the reservoir are formed as a single unit.

9. A method of using a manual breast pump, the method comprising:

engaging a breast cup of the manual breast pump with a mother's breast;

compressing and releasing a reservoir of the manual breast pump at a first location to create a first suction force to extract milk from the mother's breast into the reservoir, wherein the reservoir is defined by a wall, wherein the wall of the reservoir is thickest toward a bottom of the reservoir and thinnest toward a top of the reservoir with a continuous gradual thickening of the wall from the top of the reservoir toward the bottom of the reservoir, wherein the reservoir comprises at least two rings around the outer perimeter of the reservoir to add thickness to the wall of the reservoir, wherein a ring of the at least two rings is located toward the bottom of the reservoir, and wherein the wall of the reservoir is thickest at the ring; and compressing and releasing the reservoir at a second location to create a second suction force to extract milk from the mother's breast into the reservoir, wherein the first suction force and the second suction force are different.

10. The method of claim 9, wherein the first location is located closer to a top of the reservoir than the second location, and wherein the first suction force is greater than second suction force.

11. The method of claim 9, wherein the first location is located closer to a bottom of the reservoir than the second location, and wherein the first suction force is less than the second suction force.

12. The method of claim 9, further comprising folding down the breast cup prior to engaging the breast cup with the mother's breast.

13. The method of claim 12, further comprising returning the breast cup to its original shape after engaging the breast cup with the mother's breast.

* * * * *